United States Patent [19]

Yamashita et al.

[11] Patent Number: 4,764,206

[45] Date of Patent: Aug. 16, 1988

[54] CONTRADEGLUTITIOUS SOLID HERBICIDAL COMPOSITION

[75] Inventors: Kazuhiro Yamashita; Mamoru Yoshida, both of Tokyo, Japan

[73] Assignee: S D S Bioteck K.K., Tokyo, Japan

[21] Appl. No.: 829,037

[22] Filed: Feb. 13, 1986

Related U.S. Application Data

[63] Continuation-in-part of Ser. No. 786,025, Oct. 10, 1985, abandoned.

[51] Int. Cl.$^4$ ............................................. A01N 25/32
[52] U.S. Cl. ..................................... 71/94; 71/DIG. 5
[58] Field of Search ............................... 71/94, DIG. 5

[56] References Cited

U.S. PATENT DOCUMENTS

| | | | |
|---|---|---|---|
| 3,920,448 | 11/1975 | Albert et al. | 71/92 |
| 4,183,740 | 1/1980 | Jang et al. | 71/92 |
| 4,401,456 | 8/1983 | Connick Jr. | 71/88 |
| 4,432,787 | 2/1984 | Milianis et al. | 71/94 |

FOREIGN PATENT DOCUMENTS 1395502 6/1972 United Kingdom.
1506568 4/1978 United Kingdom.

OTHER PUBLICATIONS

Barrett, Pesticide Science, vol. 9 (1978), pp. H25–H33.
Tanner et al. Chem. Abstr., vol. 102 (1985), 1898k.

*Primary Examiner*—Catherine L. Mills
*Attorney, Agent, or Firm*—Sughrue, Mion, Zinn, Macpeak, and Seas

[57] ABSTRACT

A contradeglutitious solid herbicidal composition comprising a 1,1'-dimethyl-4,4'-bipyridylium salt in a substantially solid state and a thickening agent and, optionally, a water absorbable inorganic fine powder. This composition is difficult to swallow in its original form or even when diluted in a glass of water. The composition does not impair the inherent herbicidal effects and applicability of paraquat.

7 Claims, No Drawings

CONTRADEGLUTITIOUS SOLID HERBICIDAL COMPOSITION

CROSS-REFERENCE TO RELATED APPLICATION

This application is a continuation-in-part of Ser. No. 786,025, filed Oct. 10, 1985 now abandoned.

BACKGROUND OF THE INVENTION

1. Field of the Invention

The present invention relates to a contradeglutitious solid herbicidal composition (i.e., a herbicidal composition not easy to swallow). More specifically, it relates to a contradeglutitious solid herbicidal composition containing, as a herbicidal agent, a "1,1'-dimethyl-4,4'-bipyridylium" salt (i.e., so-called "paraquat" salt), which is not easily swallowed even if such a paraquat salt solution is accidentally or intentionally drunk. The term "paraquat" used herein means 1,1'-dimethyl-4,4'-bipyridinium cation.

2. Description of the Related Art

The importance of herbicides or pesticides in modern agriculture is widely recognized and many herbicides or pesticides are in practical use. Herbicides or pesticides practically used must be registered, after being subjected to a severe examination including the toxicity and safety thereof based on the laws and regulations concerned. Accordingly, as long as herbicides or pesticides are properly used according to instructions for use, they will not harm the human body in any way. However, the present status is such that toxic or poisonous accidents caused by a portion of herbicides or pesticides still occur in spite of the fact that the proper handling of herbicides or pesticides and the preventing of injury thereby to the human body has been taught and the dangers of improper usage have been widely announced for a long time. In particular, a herbicide, a paraquat salt, is widely used because of the strong herbicidal effect and easy applicability thereof, and quite a large number of toxic or poisonous accidents have been caused by the accidental or intentional drinking of the paraquat salt despite clear indications of its toxicity. This is because paraquat has very strong acute toxicity and is commercially available in the form of an aqueous solution having a relatively high concentration.

Paraquat is generally marketed as an about 24 W/V % aqueous paraquat dichloride solution. When used, the raw paraquat solution is diluted 300 to 1500 times with water and the resultant diluted paraquat solution is generally sprayed as a weed-killer in an amount of 100 to 150 liters per 10 are (i.e., 100 m$^2$). The oral acute toxicity of paraquat dichloride is an LD$_{50}$ of 166 to 217 mg/kg (rat) and it is reported in "Kyukyu Igaku" 4(4), p 399 (1980) that the lethal dose of paraquat for humans is approximately 15 ml of the 20% aqueous paraquat solution (i.e., approximately 3 g of paraquat). On the other hand, it is reported in "Gekkan Yakuji" 25(8), p 147 (1983) that an average amount drunk in one mouthful by an adult human is generally approximately 40 ml. This means that, if a commercially available paraquat solution is accidentally or intentionally drunk, a mouthful of the paraquat solution is sufficient to be lethal to a human.

Various attempts have been made to prevent accidental toxic or poisonous injury caused by paraquat. For example, odorants or colorants are mixed into the paraquat solutions to prevent accidental drinking by giving it an unpleasant odor or color. However, this is not effective for infants or against intentional drinking. Furthermore, the inclusion of nauseants in the paraquat solutions has been proposed, to rapidly remove the mistakenly drunk paraquat from the stomach and other digestive system prior to the absorbance of paraquat into the body therethrough. However, it is extremely unfortunate that, at present, once paraquat is swallowed, a reliable and effective curing or treatment method is not available, although this depends upon the amount swallowed, even if the paraquat is vomitted at an early stage.

Consequently, although various attempts have been made to solve the above-mentioned problems, an appropriate and effective means has not, as yet, been found. In order to prevent toxic or poisonous accidents caused by the oral intake of paraquat, it is thought that the concentration of commercially available paraquat should be decreased so that a lethal amount is not reached unless a relatively large amount of a paraquat solution is drunk. However, this causes disadvantages in the transportation and storage of paraquat solutions and also impairs the inherent easy handling characteristics of paraquat. On the other hand, it is considered that, when paraquat is marketed in the form of a solid instead of an aqueous solution, the paraquat becomes difficult to drink, toxic or poisonous injuries caused by the accidental intake of paraquat can be prevented, and, furthermore, the transportation and storage thereof are convenient. However, since paraquat is completely soluble in water, an aqueous solution containing a lethal amount of paraquat is easily prepared from such solid paraquat by the addition of, for example, a mouthful of water, and thus it is practically impossible to prevent a person with suicidal intent from taking the poison.

SUMMARY OF THE INVENTION

Accordingly, the objects of the present invention are to eliminate the above-mentioned disadvantages of paraquat and to provide a contradeglutitious solid herbicidal composition capable of effectively preventing the occurrence of accidents or injuries from acute poisoning caused by an accidental or intentional intake of paraquat, without impairing the essential characteristics, e.g., strong herbicidal effects and easy applicability, of paraquat.

Other objects and advantages of the present invention will be apparent from the following description.

In accordance with the present invention, there is provided a contradeglutitious solid herbicidal composition comprising a 1,1'-dimethyl-4,4'-bipyridylium salt in a substantially solid state and a thickening agent.

DESCRIPTION OF THE PREFERRED EMBODIMENTS

According to the present invention, since the herbicidal composition is in a solid form and contains a thickening agent, it is difficult to swallow in the solid form itself and, if an amount of the composition corresponding to a lethal dose to human beings is dissolved in a glass of water, only a non-fluidizable mixture, which is difficult to swallow, is obtained. Of course, the present solid herbicidal composition can be changed to an aqueous solution by diluting the composition with a large amount of water. However, since the paraquat concentration of this diluted solution is very low, a lethal amount cannot be ingested unless a remarkably large amount of the diluted solution is drunk. This is practically difficult and the effects of nauseants can be utilized to decrease the likelihood of death from such ingestion. Furthermore, since the present solid herbicidal composition can be stored and transported in glass and plastic vessels, and since the present solid herbicidal composition can be used on-site by diluting with water, there is no substantial difference between the present solid herbicidal composition and conventional commercially available paraquat solutions in the transportation, handling, and applicability thereof. When diluting the present solid herbicidal composition with a large amount of water for use on-site, the present solid herbicidal composition becomes a low viscosity solution suitable for spraying.

Furthermore, the solid herbicidal composition according to the present invention may optionally contain, in addition to the essential paraquat and thickening agent, various conventional ingredients such as colorants, odorants, and nauseants, to further improve the safety thereof. In addition, surfactants and other herbicidal active components also can be included in the present herbicidal composition to improve the herbicidal effects and the applicability of the herbicidal composition.

The paraquat usable in the present herbicidal composition is substantially in the form of a solid. Accordingly, 1,1'-dimethyl-4,4'-bipyridylium salts (e.g., dichloride, dibromide, and bismethylsulfate or the complex salts with, for example, manganese, iron, urea, thiourea, p-aminophenol, catechol) in the form of crystals can be directly mixed with the thickening agent. However, the industrially or commercially available aqueous paraquat solutions also can be used in the preparation of the present solid herbicidal composition by adding a water-absorbing inorganic fine powder to form an apparently water-free fluidizable solid paraquat prior to mixing with the thicking agent. Any water-absorbing inorganic fine powder can be used for this purpose so long as the herbicidal effects of the paraquat and the characteristics of the thickening agents are not adversely affected. Examples of such water-absorbing inorganic fine powders are white carbon, diatomaceous earth, finely divided calcium silicate, perlite, calcined kaoline, and zeolite. These can be used alone or in any mixture thereof. There are no critical limitations to the addition amount of the water-absorbing inorganic fine powder, as long as the paraquat solution can be substantially solidified. For example, when an about 40% aqueous paraquat dichloride solution is used, an equal amount or more, based on the amount of the water contained in the paraquat dichloride solution, of the inorganic powder is generally used in the case of, for example, white carbon, finely divided calcium silicate, and perlite, and two times or more, based on the amount of the water contained in the paraquat dichloride solution, of the inorganic powder in generally used in the case of, for example, diatomaceous earth, calcined kaoline, and zeolite. Although there is no critical limitation to the upper limit of the amount of the inorganic powder, generally speaking, the maximum amount of the inorganic powder is ten times the amount of water in the paraquat dichloride solution, mainly from an economical viewpoint.

There are no critical limitations to the paraquat concentration of the present solid herbicidal compositions. However, when the paraquat concentration is too low, only a small dilution ratio of the composition with water is required to obtained the desired concentration when spraying on-site and, therefore, spraying tends to become difficult from the standpoint of both the viscosity and the spraying amount, and the efficiency of the transportation and storage also tends to be decreased. On the other hand, when the paraquat concentration in the present herbicidal composition is too high, the above-mentioned problems do not arise but the allowable safety range tends to become small from the point of view of preventing the possible occurrence of toxic or poisonous accidents. For these reasons, the practically preferable concentration range of the paraquat in the present herbicidal compositions is from about 3% by weight to 30% by weight.

The thickening agents usable in the present invention are those which are capable of increasing the viscosity or forming the gel with the addition of a relatively small amount of water to the solid herbicidal composition at an ambient temperature in a short period of time. There are no specific limitations to the types of the thickening agents as long as the above-mentioned requirements are fulfilled. Various natural and synthetic thickening agents can be used in the present invention. Typical examples of such thickening agents are alginic acid salts, propylene glycol alginates; carrageenan, guar gum, modified guar gum, xanthan gum, modified xanthan gum, carboxymethyl cellulose salts, methyl cellulose, hydroxyalkyl cellulose, pectine, locust bean gum, carboxymethyl starch salts, pullulan, polyvinyl alcohol, polyvinyl pyrrolidone, polyacrylic acid salts, and polyacryl amide. These thickening agents may be used alone or in any mixture thereof. Furthermore, various conventional acids or salts also may be used in the present herbicidal compositions to further improve the gellation or thickening characteristics of the present solid herbicidal composition. The addition of inorganic salts to the present herbicidal composition can further improve the gellation properties of the present herbicidal compositions.

There are no definite concentrations of the thickening agents in the present herbicidal compositions since the concentrations largely depend upon the type of thickening agent and the concentration of the paraquat component. As one practical measure, the thickening agent can be used in an amount such that the herbicidal compositions causes gellation, when approximately 3 g (i.e., the above-explained lethal dose of paraquat for humans) or more, in terms of paraquat cation, of the herbicidal composition according to the present invention is diluted with approximately 40 ml of water (i.e., the above-explained average amount drunk in one mouthful by an adult human). That is, when the paraquat concentration of the present solid herbicidal composition is 3% to 30% by weight, the thickening agent can be added in an amount such that all of the composition becomes a high viscous liquid or gel that cannot be easily swallowed when the present herbicidal composition is diluted with a four-tenths (4/10) amount of water in the case of a paraquat concentration of 3%, to 4 times the amount of water in the case of a paraquat concentration of 30%. Furthermore, the concentration of the thickening agent in the present herbicidal composition should be such that the composition becomes an easily sprayable low viscosity liquid when the composition is diluted with water for practical use. Thus, generally speaking, the thickening agent can be added to the present herbicidal composition in an amount such that the composition becomes an easily sprayable low viscosity liquid for practical use, when the composition is diluted with 50 times the amount of water in the case of a paraquat concentration of 3%, to 500 times the amount of water in the case of a paraquat concentration of 30%. More specifically, the concentration of the thickening agent in the present herbicidal concentration is preferably more than 0.5 times but less than 15 times, more preferably 0.6 times to 12 times, of the amount of the paraquat (i.e., cation) in the composition, although the concentration depends upon the type of thickening agent used.

The solid herbicidal composition according to the present invention may further contain, as an optional component, conventional colorants, odorants, nauseants, and the like to improve the safety of the paraquat herbicide as well as surfactants and other herbicidal active components to improve the herbicidal effects. However, it should be noted that these optional components should be added in such an amount that the herbicidal effects and the other characteristics of the present composition are not adversely affected.

EXAMPLES

The present invention will be further explained by, but is by no means limited to, the following Examples and Test Examples. In the Examples, "parts" and "%" are all by weight unless otherwise specified.

EXAMPLE 1 to 7

Paraquat wettable powders were prepared by uniformly mixing and grinding solid paraquat components and other ingredients in the following formulation ratios:

| | | |
|---|---|---|
| (1) | Paraquat dichloride | 25 parts |
| | Sodium carboxymethyl-starch | 75 parts |
| | (PRIMOJEL ®: Matsutani Kagaku Kogyo Co., Ltd.) | |
| (2) | Paraquat dichloride | 25 parts |
| | Guar gum | 35 parts |
| | (EMCO GUM ® CSA 200/50: Meyhall Chemical A.G.) | |
| | White carbon | 40 parts |
| | (CARPLEX ® #80: Shionogi & Co., Ltd., hereinbelow "white carbon") | |
| (3) | Paraquat dichloride | 15 parts |
| | Pullulan | 60 parts |
| | (PULLULAN ® PF30: Hayashibara Seibutsukagaku Kenkyusho K.K.) | |
| | White carbon | 20 parts |
| | Surfactant (Polyoxyethylene nonylphenyl ether) | 5 parts |
| (4) | Paraquat dichloride | 15 parts |
| | Polyvinyl pyrrolidone | 60 parts |
| | (Polyvinyl pyrrolidone PVP K-90: Wako Pure Chemical Industries, Ltd.) | |
| | White carbon | 20 parts |
| | Surfactant | 5 parts |
| | (Polyoxyethylene higher aliphatic alcohol ether) | |
| (5) | Paraquat dichloride | 15 parts |
| | Carboxymethyl starch | 60 parts |
| | (Solvitose ® C-5: Matsutani Kagaku Kogyo Co., Ltd.) | |
| | White carbon | 20 parts |
| | Surfactant | 5 parts |
| | (Polyoxyethylene alkylamine) | |
| (6) | Paraquat dichloride | 25 parts |
| | Xanthan gum | 20 parts |
| | (KELZAN ®: Kelco Division of Merck, hereinbelow "Xanthan gum") | |
| | White carbon | 30 parts |
| | Surfactant | 5 parts |
| | (Polyoxyethylene nonylphenyl ether) | |
| | Foaming agent malic acid | 10 parts |
| | sodium bicarbonate | 10 parts |
| (7) | Paraquat dimethylsulfate | 30 parts |
| | Xanthan gum | 40 parts |
| | White carbon | 25 parts |
| | Surfactant | 5 parts |
| | (Polyoxyethylene nonylphenyl ether) | |

EXAMPLES 8 to 21

Paraquat wettable powders were prepared by first adding the water-absorbable inorganic fine powder listed below to a concentrated paraquat solution (i.e., aqueous solution containing 37% by weight of paraquat dichloride) to form a solid mixture, followed by the addition of the other ingredients in the following formulation ratios. The resultant mixtures were uniformly mixed and ground.

| | | |
|---|---|---|
| (8) | Concentrated paraquat solution | 27 parts |
| | Sodium alginate | 45 parts |
| | (KELGIN ® HV: Kelco Division of Merck) | |
| | White carbon | 23 parts |
| | Surfactant | 5 parts |
| | (Polyoxyethylene nonylphenyl ether) | |
| (9) | Concentrated paraquat solution | 40 parts |
| | Propylene glycol alginate | 20 parts |
| | (KIMIROID ® HV: Kimitsu Kagaku Kogyo K.K) | |
| | White carbon | 35 parts |
| | Surfactant | 5 parts |
| | (Polyoxyethylene nonylphenyl ether) | |
| (10) | Concentrated paraquat solution | 27 parts |
| | Carrageenan | 45 parts |
| | (TAKARAGEN ® G50: Takagen Corporation) | |
| | White carbon | 23 parts |
| | Surfactant | 5 parts |
| | (Polyoxyethylene nonylphenyl ether) | |
| (11) | Concentrated paraquat solution | 40 parts |
| | Guar gum | 15 parts |
| | (EMCO GUM ® CSA 200/50) | |
| | White carbon | 35 parts |
| | Surfactant | 5 parts |
| | (Polyoxyethylene nonylphenyl ether) | |
| | Nauseant | 1 part |
| | (Emetine hydrochloride) | |
| | Odorant | 4 parts |
| | ($\beta$-Phenethyl alcohol) | |
| (12) | Concentrated paraquat solution | 40 parts |
| | Modified guar gum | 15 parts |
| | (JAGUAR ® HP-8: Meyhall Chemical AG) | |
| | White carbon | 35 parts |
| | Surfactant | 5 parts |
| | (Polyoxyethylene nonylphenyl ether) | |
| | Nauseant | 1 part |
| | (Tartar emetic) | |
| | $\beta$-Phenethyl alcohol | 4 parts |
| (13) | Concentrated paraquat solution | 40 parts |
| | Xanthan gum | 15 parts |
| | (KELZAN ®) | |
| | White carbon | 30 parts |
| | Surfactant | 5 parts |
| | (Polyoxyethylene nonylphenyl ether) | |
| | Anhydrous sodium sulfate | 10 parts |
| (14) | Concentrated paraquat solution | 27 parts |
| | Sodium carboxymethyl cellulose | 45 parts |
| | (SUNROSE ® SN 20TC: Sanyo Kokusaku Pulp Co., Ltd.) | |
| | White carbon | 23 parts |
| | Surfactant | 4 parts |
| | (Polyoxyethylene nonylphenyl ether) | |
| (15) | Concentrated paraquat solution | 50 parts |
| | Methyl cellulose | 10 parts |
| | (MAPOROSE ® M-10000: Matsumoto Yushi Seiyaku K.K.) | |
| | White carbon | 36 parts |
| | Surfactant | 4 parts |
| | (Polyoxyethylene nonylphenyl ether) | |
| (16) | Concentrated paraquat solution | 20 parts |

-continued

|  |  |  |
|---|---|---|
| Sodium carboxymethyl starch (PRIMOJEL ®) | 57 parts | |
| White carbon | 18 parts | |
| Surfactant (Polyoxyethylene nonylphenyl ether) | 5 parts | |
| (17) Concentrated paraquat solution | 27 parts | |
| Polyvinyl alcohol (PVA 117S: Kuraray Co., Ltd.) | 45 parts | |
| White carbon | 23 parts | |
| Surfactant (Polyoxyethylene nonylphenyl ether) | 5 parts | |
| (18) Concentrated paraquat solution | 40 parts | |
| Polyacrylamide (VISCOMATE ® NS: Showa Denko K.K.) | 24 parts | |
| White carbon | 31 parts | |
| Surfactant (Polyoxyethylene nonylphenyl ether) | 5 parts | |
| (19) Concentrated paraquat solution | 27 parts | |
| Pectin (GENU PECTIN BB RAPID SET; he Copenhagen | 45 parts Pectin Factory Ltd.) | |
| White carbon | 23 parts | |
| Surfactant (Polyoxyethylene nonylphenyl ether) | 5 parts | |
| (20) Concentrated paraquat solution | 40 parts | |
| Xanthan gum (KELZAN ®) | 14 parts | |
| Locust bean gum (MEYPRODYN ® 200: Meyhall Chemical AG) | 10 parts | |
| White carbon | 31 parts | |
| Surfactant (Polyoxyethylene nonylphenyl ether) | 5 parts | |
| (21) Concentrated paraquat solution | 40 parts | |
| Xanthan gum (KELZAN ®) | 18 parts | |
| Diatomaceous earth (RADIOLITE: Showa Kagaku K.K.) | 37 parts | |
| Surfactant (Polyoxyethylene nonylphenyl ether) | 5 parts | |

EXAMPLE 22

Paraquat wettable granules were prepared as follows.

Of the following ingredients, the concentrated paraquat solution used in Examples 8 to 21 was mixed with white carbon to form a solid mixture, followed by mixing the other ingredients. The resultant mixture was uniformly mixed and ground, and then granulated by spraying water containing 2% of PVP K-90 in a fluid bed type granulator.

| | |
|---|---|
| Concentrated Paraquat solution | 54 parts |
| Guar gum (EMCO GUM ® CSA 200/50) | 9 parts |
| White carbon (CARPLEX ® #80) | 34 parts |
| Surfactant (Polyoxyethylene nonylphenyl ether) | 3 parts |

The resultant paraquat wettable granules, after drying in the fluid bed, had the following composition.

| | |
|---|---|
| Paraquat dichloride | 30 parts |
| Guar gum | 14 parts |
| White carbon | 51.5 parts |
| Surfactant | 4.5 parts |

EXAMPLES 23 to 25

Paraquat wettable powders having the following compositions were prepared by mixing the concentrated aqueous paraquat dichloride solution with white carbon to form a solid mixture. The resultant solid mixture was uniformly mixed with the other ingredients, followed by drying to evaporate the water from the mixture.

| | |
|---|---|
| (23) Paraquat dichloride | 35 parts |
| Guar gum (EMCO GUM ® CSA 200/50) | 23 parts |
| White carbon | 42 parts |
| (24) Paraquat dichloride | 35 parts |
| Carrageenan (TAKARAGEN: Takagen Corporation) | 23 parts |
| White carbon | 42 parts |
| (25) Paraquat dichloride | 35 parts |
| Xanthan gum (KELZAN ®) | 23 parts |
| White carbon | 42 parts |

TEST EXAMPLE 1

A 30 g amount of the solid composition prepared in Example 1 was mixed with 150 ml of water while stirring so as to obtain a mixture having a paraquat dichloride concentration of 5%. The mixture became pasty shortly after the water was added. Thus, a pasty mixture, which is impossible to swallow, was obtained. On the other hand, the paraquat dichloride composition prepared in Example 1 was diluted with water in such a ratio that 50 g of the effective component was included in 150 liters of the diluted composition. The diluted herbicidal composition thus obtained was sprayed under pressure onto foliage (or stems and leaves) of crabgrass, purple nutsedge, common lambsquarter, pigweed, and barnyard millet, grown in test pots, by using a pressure type atomizer in such an amount that 50 g of the active component per 10 are was applied. Prior to the spraying, a conventional nonionic type spreading agent was added to the herbicidal composition.

During the spraying, clogging of the spray nozzle of the atomizer did not occur. When the herbicidal effects were compared with those of commercially available paraquat dichloride solution 5 days after the treatment, no substantial difference was observed.

TEST EXAMPLE 2

A 50 g amount of the solid composition prepared in Example 11 was mixed with 150 ml of water while stirring so as to obtain a mixture having a paraquat dichloride concentration of 5%. The mixture became pasty shortly after the water was added. Thus, a pasty mixture, which is impossible to swallow, was obtained.

On the other hand, the paraquat dichloride composition prepared in Example 11 was diluted with water in such a ratio that 50 g of the effective component was included in 150 liters of the diluted composition. The diluted herbicidal composition thus obtained was sprayed under pressure onto the foliage of crabgrass, purple nutsedge, common lambsquarter, pigweed, and barnyard millet grown in test pots, by using a pressure type atomizer in such an amount that 50 g of the active component per 10 are was applied. Prior to the spraying, a conventional nonionic type spreading agent was added to the herbicidal composition.

During the spraying, clogging of the spray nozzle of the atomizer did not occur. When the herbicidal effects were compared with those of a commercially available paraquat dichloride solution 5 days after the treatment, no substantial difference was observed.

TEST EXAMPLE 3

A 50 g amount of the solid composition prepared Example 13 was mixed with 150 ml of water while stirring so as to obtain a mixture having a paraquat dichloride concentration of 5%. The mixture became pasty shortly after the water was added. Thus, a pasty mixture, which is impossible to swallow, was obtained.

On the other hand, the paraquat dichloride composition prepared in Example 13 was diluted with water in such a ratio that 50 g of the effective component was included in 150 liters of the diluted composition. The diluted herbicidal composition thus obtained was sprayed under pressure onto the foliage of crabgrass, purple nutsedge, common lambsquarter, pigweed, and barnyard millet grown in test pots, by using a pressure type atomizer in such an amount that 50 g of the active component per 10 are was applied. Prior to the spraying, a conventional nonionic type spreading agent was added to the herbicidal composition.

During the spraying, clogging of the spray nozzle of the atomizer did not occur. When the herbicidal effects were compared with those of a commercially available paraquat dichloride solution 5 days after the treatment, no substantial difference was observed.

TEST EXAMPLE 4

A 40 g amount of the solid composition prepared in Example 15 was mixed with 150 ml of water while stirring so as to obtain a mixture having a paraquat dichloride concentration of 5%. The mixture became pasty shortly after the water was added. Thus, a pasty mixture, which is impossible to swallow, was obtained.

On the other hand, the paraquat composition prepared in Example 15 was diluted with water in such a ratio that 50 g of the effective component was included in 150 liters of the diluted composition. The diluted herbicidal composition thus obtained was sprayed under pressure onto the foliage of crabgrass, purple nutsedge, common lambsquarter, pigweed, and barnyard millet grown in test pots, by using a pressure type atomizer in such an amount that 50 g of the active component per 10 are was applied. Prior to the spraying, a conventional nonionic type spreading agent was added to the herbicidal composition.

During the spraying, clogging of the spray nozzle of the atomizer did not occur. When herbicidal effects were compared with those of a commercially available paraquat dichloride solution 5 days after the treatment, no substantial difference was observed.

TEST EXAMPLE 5

The herbicidal effects of the paraquat dichloride wettable powders obtained in Examples 23 to 25 were evaluated in an agricultural field. As Reference Examples, a 24% aqueous paraquat dichloride solution and a 32% bialaphos liquid agent were used. The weeds used for the test were crabgrass having a height of 25 to 30 cm, smartweed having a height of 50 cm, common lambsquarter having a height of 50 cm, and pigweed having a height of 25 cm.

The area in each test was 1.5 m×2 m (i.e., 3 m²). The diluted herbicidal composition samples containing 0.3% of a surfactant were sprayed by using a pressure type spray atomizer at an active component amount of 0.5 or 1 kg A.I. (i.e., active ingredient)/ha and at a spraying water amount of 1000 l/ha.

Six days after the spraying, the herbicidal effects were observed according to the following standard
0 ... No effect
100 ... Complete kill The results are as shown in Table 1. As is clear from the results shown in Table 1, since the grass height at the time of the treatment is relatively large, complete killing was not obtained at a rate of 0.5 kg A.I./ha. However, in the case of 1.0 kg A.I./ha, good results were obtained and there was no substantial difference between the compositions of Examples 23 and 25 and the conventional paraquat dichloride solution.

TABLE 1

| Sample Composition No. | Rate (kg A.I./ha) | Weed Control | | | |
|---|---|---|---|---|---|
| | | Crabgrass | Smartweed | Lambsquarter | Pigweed |
| Example No. 23 | 0.5 | 60 | 93 | 70 | 80 |
| | 1.0 | 95 | 95 | 100 | 100 |
| Example No. 24 | 0.5 | 85 | 85 | 90 | 93 |
| | 1.0 | 98 | 100 | 100 | 100 |
| Example No. 25 | 0.5 | 90 | 90 | 90 | 98 |
| | 1.0 | 90 | 100 | 100 | 100 |
| Paraquat dichloride | 0.5 | 80 | 75 | 85 | 95 |
| | 1.0 | 93 | 98 | 100 | 100 |
| Bialaphos | 0.5 | 60 | 93 | 70 | 80 |
| | 1.0 | 95 | 90 | 100 | 100 |
| Control (No treatment) | — | 0 | 0 | 0 | 0 |

We claim:

1. A method for making a lethal amount of a 1,1'-dimethyl-4,4'-bipyridylium salt (i.e., a paraquat salt), non-swallowable by formulating a composition comprising the paraquat salt in a substantially solid state and a thickening agent inocorprated thereinto, the amount of said thickening agent being such that the composition becomes a non-swallowable high viscous liquid or gel upon the addition of water to the composition in such a relationship that the composition becomes a non-swallowable liquid or gel when the composition is diluted with a four-tenths amount of water, based on the amount of the composition, in the case of a paraquat concentration in the composition of 3% by weight, to 4 times the amount of water, based on the amount of the composition, in the case of a paraquat concentration in the composition of 30% by weight and that the composition becomes an easily sprayable low viscosity liquid upon the addition of water to the composition in such a relationship that the composition becomes an easily sprayable liquid when the composition is diluted with 50 times the amount of water, based on the amount of the composition, in the case of a paraquat concentration in the composition of 3% by weight, to 500 times the amount of water, based on the amount of the composition, in the case of a paraquat concentration in the composition of 30% by weight.

2. A method as claimed in claim 1, wherein said composition further comprises a water absorbable inorganic fine powder capable of converting an aquous 1,1'dimethyl-4,4'-bipyridylium salt solution into a solid state.

3. A method as claimed in claim 2, wherein said water absorbable inorganic fine powder is at least one member selected from the group consisting of white carbon, diatomaceous earth, finely divided calcium silicate, perlite, calcined kaoline, and zeolite.

4. A method as claimed in claim 1, wherein said thickening agent is at least one agent selected from the group consisting of alginic acid salts, propylene gylcol alginates, carrageenan, guar gum, modified guar gum, xanthan gum, modified xanthan gum, carboxymethyl cellulose salts, methyl cellulose, hydroxyalkyl cellulose, pectine, locust bean gum, carboxymethyl starch salts, pullulan, polyvinyl alcohol, polyvinyl pyrrolidone, polyacrylic acid salts, and polyacryl amide.

5. A method as claimed in claim 1, wherein the amount of 1,1'-dimethyl-4,4'-bipyridylium cation in the composition is 3% to 30% by weight.

6. A method as claimed in claim 1, wherein the amount of the thickening agent is more than 0.5 times but less than 15 times the amount of the paraquat in the composition.

7. A method as claimed in claim 1, wherein said composition further comprises a surfactant and a nauseant.

* * * * *